(12) United States Patent
Yamada et al.

(10) Patent No.: US 12,064,509 B2
(45) Date of Patent: Aug. 20, 2024

(54) ENEMA FOR RECTAL APPLICATION

(71) Applicant: Dr. Falk Pharma GmbH, Freiburg (DE)

(72) Inventors: Yoji Yamada, Tokyo (JP); Syoji Kondo, Tokyo (JP); Toshifumi Kajioka, Tokyo (JP)

(73) Assignee: Dr. Falk Pharma Gmbh, Freiburg (DE)

( * ) Notice: Subject to any disclaimer, the term of this patent is extended or adjusted under 35 U.S.C. 154(b) by 201 days.

(21) Appl. No.: 17/581,354

(22) Filed: Jan. 21, 2022

(65) Prior Publication Data

US 2022/0142921 A1  May 12, 2022

Related U.S. Application Data

(63) Continuation of application No. 15/546,476, filed as application No. PCT/JP2015/070667 on Jul. 21, 2015, now abandoned.

(51) Int. Cl.
| | |
|---|---|
| *A61K 9/12* | (2006.01) |
| *A61K 9/00* | (2006.01) |
| *A61K 9/08* | (2006.01) |
| *A61K 31/58* | (2006.01) |
| *A61P 1/00* | (2006.01) |

(52) U.S. Cl.
CPC .............. *A61K 9/12* (2013.01); *A61K 9/0031* (2013.01); *A61K 9/08* (2013.01); *A61K 31/58* (2013.01); *A61P 1/00* (2018.01)

(58) Field of Classification Search
CPC ........ A61K 31/58; A61K 9/0031; A61K 9/08; A61K 9/12; A61P 1/00; B01D 35/02; B05C 11/10; B05C 11/1002; B05C 11/1039; B05C 5/0225; F04B 23/06; F04B 43/08; F04B 43/088; F04B 45/02; F04B 45/06; F04B 49/007; F04B 49/22; F04B 53/20; G03F 7/16; G03F 7/162; H01L 21/67017; H01L 21/6715
See application file for complete search history.

(56) References Cited

U.S. PATENT DOCUMENTS

| | | |
|---|---|---|
| 5,914,122 A | 6/1999 | Otterbeck et al. |
| 8,476,233 B2 | 7/2013 | Pravda |
| 8,916,546 B2 | 12/2014 | Pravda |
| 2014/0135299 A1 | 5/2014 | Palepu et al. |
| 2014/0349982 A1 | 11/2014 | Forbes et al. |

FOREIGN PATENT DOCUMENTS

| | | |
|---|---|---|
| WO | 2014189955 A1 | 11/2014 |
| WO | 2018122086 A1 | 7/2018 |

OTHER PUBLICATIONS

Caprilli (Treatment of inflammatory bowel diseases: To heal the wound or to heal the sick?, Journal of Crohn's and Colitis, 2012, 6, 621-625).*
International Search Report for Application No. PCT/JP2015/070667 dated Sep. 6, 2015.
Mikihiro Fuji Ya, et al., Mucosal healing in ulcerative colitis, The Japanese Journal of Gastro-enteroloy, 2013, pp. 1900-1908 (table 2), vol. 110.
Naganuma, et al., Twice-daily Budesonide 2-mg Foam Induces Complete Mucosal Healing in Patients with Distal Ulcerative Colitis, Journal of Crohn's and Colitis, Nov. 16, 2015, pp. 828-836, vol. 10, Issue 7.
Lindgren, et al., Effect of Budesonide Enema on 1-6 Remission and Relapse Rate in Distal Ulcerative Colitis and Proctitis, Scand. J. Gastroenterol. 2002, pp. 705-710, vol. 37, Issue 6.
Public Assessment Report of the Medicines Evaluation Board in the Netherlands: Budenofalk Schuim 2 mg, rectal foam, College ter Beoordeling van Geneesmiddelen, Medicines Information Bank, Dec. 6, 2012.

* cited by examiner

*Primary Examiner* — Kevin E Weddington
(74) *Attorney, Agent, or Firm* — CURATOLO SIDOTI & TRILLIS CO., LPA; Floyd Trillis, III; Salvatore A. Sidoti

(57) ABSTRACT

Provided is an enema for rectal application containing budesonide as an active ingredient in order to treat inflammatory bowel disease, or to prevent a relapse. The enema for rectal application containing budesonide as the active ingredient, in which 1.5 to 2.5 mg of budesonide per dose is administered twice a day for 6 weeks in order to treat inflammatory bowel disease, or to prevent a relapse; the enema for rectal application described above, in which a dose of budesonide is 2.0 mg per dose; the enema for rectal application according to any one of the above, which is taken in order to treat ulcerative colitis or Crohn's disease, or to prevent a relapse; the enema for rectal application according to any one of the above, which has a foamy shape or a liquid shape.

8 Claims, 2 Drawing Sheets

ENEMA FOR RECTAL APPLICATION

TECHNICAL FIELD

The present invention relates to an enema for rectal application containing budesonide as an active ingredient in order to treat an inflammatory bowel disease, or to prevent a relapse. This application is a continuation of U.S. Ser. No. 15/546,476, filed Jul. 26, 2017, which is a United States national stage application of PCT/JP2015/070667, filed Jul. 21, 2015, which claims priority to Japanese Patent Application No. 2015-012723, filed on Jan. 26, 2015, the content of which is incorporated herein by reference.

BACKGROUND ART

Ulcerative colitis is a nonspecific inflammatory bowel disease of unknown cause that can cause ulcer and erosion mainly in a large intestine mucosa, and Crohn's disease is an inflammatory bowel disease of unknown cause which causes a discontinuous chronic granulomatous inflammation mainly in an entire digestive tract from an oral cavity to an anus. In any case, bloody stool, mucous and bloody stool, diarrhea, abdominal pain, and the like are common symptoms, and when the symptoms become severe, general social life is interfered. In addition, curative treatment is not established for these, and thus once these develop, these will repeat relapse and remission. Therefore, in order to improve the quality of life (QOL) of patients, it is important to maintain the remission period as long as possible.

Generally, medication treatment is done for the purpose of leading to clinical remission. Therefore, for example, in ulcerative colitis, in a case where the clinical symptoms disappear or are improved to the extent that the symptoms do not interfere with daily life, such as bloody stools disappear and a defecation frequency decreases to the extent that the defecation does not interfere with the daily life, even in a case where mucosal inflammation of the intestinal tract is not completely disappeared and mild inflammation is confirmed, it is said to be remission. However, in recent years, it is reported that in patient group with intestinal mucosa recovered normally (mucosal curing is reached), prognosis is good for a long period of time, and remission maintenance is significantly improved as compared with a patient group who has redness in intestinal mucosa or decreased vascular permeability, at the end of medication treatment (for example, refer to NPLs 1 and 2.) That is, in order to maintain the remission period as long as possible, it is important to aim not only clinical remission, but also intestinal mucosal curing, at the time of treatment in active phase.

Budesonide(+)-[(RS)-16α,17α-Butylidenedioxy-11β,21-dihydroxy-1,4-pregnadiene-3,20-dione]) is a steroid drug applied as a therapeutic agent for inflammatory bowel diseases such as ulcerative colitis and Crohn's disease. Budesonide is effective for topical administration and is generally used as an enema for rectal application for pharmaceutical foams packed with compressed gas and enema agents (refer to PTL 1). For treatment of the ulcerative colitis and the like, generally, 2 mg of budesonide is administered once a day for 6 weeks. In addition, in a patient group of ulcerative colitis, in which 2 mg of budesonide is administered twice a day (dose per day is 4 mg) for 2 weeks and then 2 mg of budesonide is administered once a day for 4 weeks, it is reported that the effect of improving a modified Mayo Disease Activity Index (MMDAI) to 0 or 1 is significantly higher than a placebo administered group (refer to PTL 2).

CITATION LIST

Patent Literature

[PTL 1] Japanese Patent (Granted) Publication No. 3421348

[PTL 2] United States Patent Application, Publication No. 2014/0349982

Non-Patent Literature

[NPL 1] Colombel, et al., GASTROENTEROLOGY, 2011, vol. 141, p. 1194-1201.

[NPL 2] Yokoyama, et al., Gastroenterology Research and Practice, 2013, vol. 2013, Article ID 192794.

SUMMARY OF INVENTION

Technical Problem

An object of the present invention is to provide an enema for rectal application in which the mucosal curing effect is significantly superior to an enema of the related art, in an enema for rectal application containing budesonide as an active ingredient in order to treat an inflammatory bowel disease, or to prevent a relapse.

Solution to Problem

As a result of intensive studies to solve the above problems, the present inventors find that the mucosal curing effect is significantly higher as compared with the case of administration once a day for 6 weeks in the related art, by administering an enema for rectal application with budesonide as an active ingredient twice a day for 6 weeks, and thus completes the present invention.

That is, an embodiment of the present invention relates to an enema for rectal application of the following [1] to [6].

[1] An enema for rectal application containing budesonide as an active ingredient, in which 1.5 to 2.5 mg of budesonide per dose is administered twice a day for 6 weeks in order to treat inflammatory bowel disease, or to prevent a relapse.

[2] The enema for rectal application according to the above [1] or 2, in which a dose of budesonide is 2.0 mg per dose.

[3] The enema for rectal application according to the above [1] or [2], which is administered in order to treat ulcerative colitis or Crohn's disease, or to prevent a relapse.

[4] The enema for rectal application according to any one of the above [1] to [3], which has a foamy shape or a liquid shape.

[5] A package of an enema for rectal application, in which the enema for rectal application according to any one of the above [1] to [4] containing 1.5 to 2.5 mg of budesonide per dose can be administered 14 times.

[6] A manufacturing method of a package of an enema for rectal application, in which the enema for rectal application according to any one of the above [1] to [4] is adjusted such that the enema for rectal application containing 1.5 to 2.5 mg of budesonide per dose can be administered 14 times.

In addition, in another aspect of the embodiment of the present invention, the following aspects are provided.

[1A] For a subject with inflammatory bowel disease or a subject after improvement of symptoms of inflammatory bowel disease, a method for a treatment or prevention of relapse of inflammatory bowel disease by transanally administrating a dose of 1.5 to 2.5 mg of budesonide twice a day for 6 weeks.

[2A] The method for the treatment or prevention of relapse of inflammatory bowel disease according to the above [1A] by administrating 2.0 mg of budesonide per dose.

[3A] The method for the treatment or prevention of relapse of inflammatory bowel disease according to the above [1A] to [2A], in which the inflammatory bowel disease is ulcerative colitis or Crohn's disease.

[4A] The method for the treatment or prevention of relapse of inflammatory bowel disease according to the above [1A] to [3A], in which in the administration, the enema for rectal application containing the budesonide is taken.

[5A] The method for the treatment or prevention of relapse of inflammatory bowel disease according to the above [4A], in which the enema for rectal application has a foamy shape or a liquid shape.

[6A] The method for the treatment or prevention of relapse of inflammatory bowel disease according to the above [1A] to [5A], in which the administration of twice a day is performed with an interval of at least 6 hours between the first and second administrations.

[1B] A composition for the treatment or prevention of relapse of inflammatory bowel disease containing 1.5 to 2.5 mg of budesonide.

[2B] The composition for the treatment or prevention of relapse of inflammatory bowel disease according to the above [1B] containing 2.0 mg of budesonide.

[3B] A package of the composition for the treatment or prevention of relapse of inflammatory bowel disease, the package containing an enema foaming agent that can be administered 14 times in a fixed dose of the composition for the treatment or prevention of relapse of inflammatory bowel disease according to the above [1B] or [2B].

[1C] Use of the composition for the treatment or prevention of relapse of inflammatory bowel disease according to the above [1B] or [2B] in the manufacture of the enema for rectal application.

Advantageous Effects of Invention

The enema for rectal application according to the present invention has remarkably high curing effect on intestinal mucosa where ulcer and erosion occur due to inflammation. Therefore, the enema for rectal application according to the present invention is extremely excellent as an enema for rectal application in order to treat inflammatory bowel disease such as ulcerative colitis and Crohn's disease or the like, or to prevent a relapse.

DESCRIPTION OF EMBODIMENTS

Figure 1:
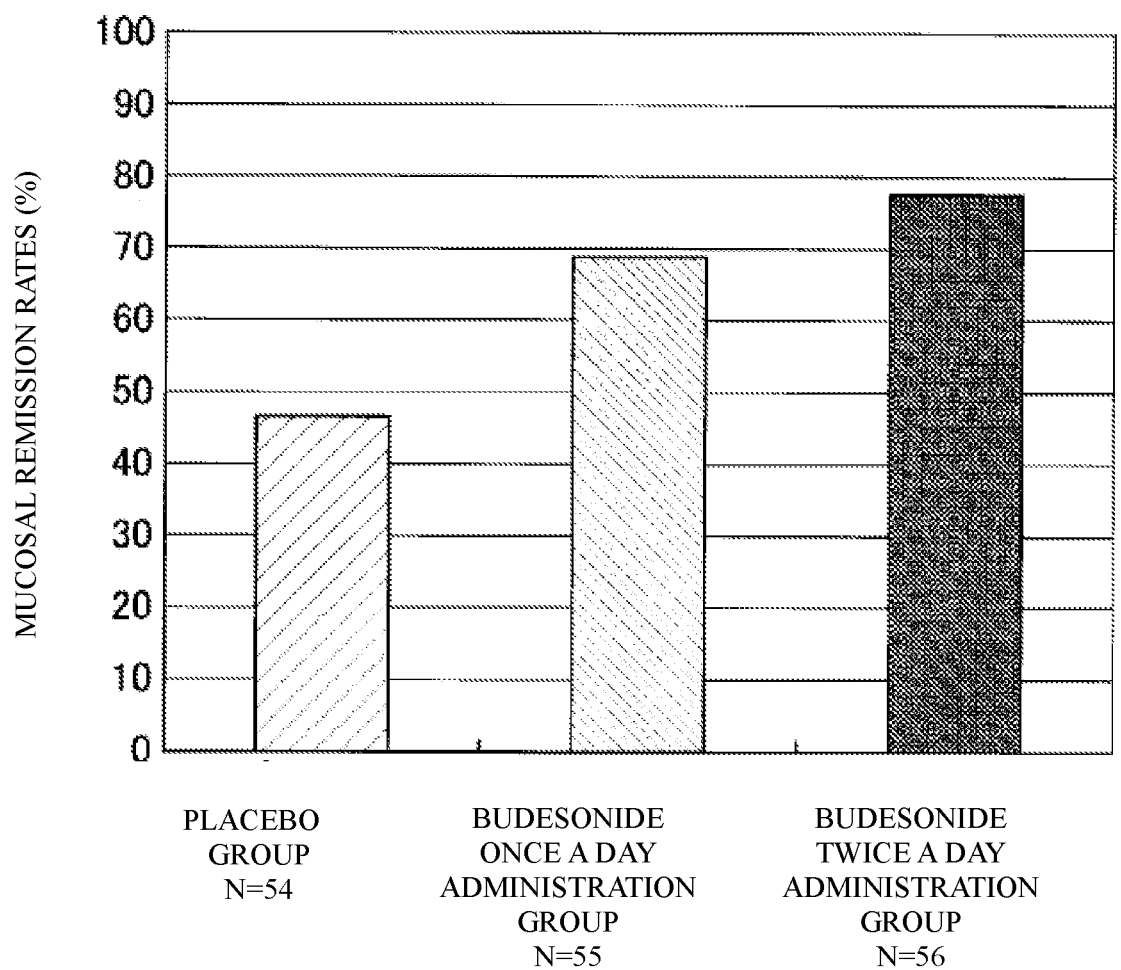
FIG. 1 is a diagram illustrating mucosal remission rates (%) of each group in Application Example 1.

Hereinafter, the present invention will be described in detail by illustrating embodiments. An enema for rectal application according to the present embodiment is administered (taken) with budesonide as an active ingredient, and 1.5 to 2.5 mg of budesonide twice a day for 6 weeks in order to treat an inflammatory bowel disease, or to prevent a relapse. In the related art, budesonide is used as a therapeutic agent for the inflammatory bowel disease by administering 2 mg once a day for 6 weeks directly to a rectum. On the contrary, although a dose and administration period per dose of the enema for rectal application according to the present embodiment are the same as those of the method of the related art, the effect of curing an inflammation of an intestinal mucosa is significantly superior to the case of taking once a day in the related art. In addition, although the dose per day of the enema for rectal application according to the present embodiment is twice as much as that of the method of the related art, the enema can be safely taken as much as the method of the related art without any special side effects as compared with the method of the related art. In the related art, there is example in which the enema for rectal application described above is administered twice a day until two weeks, but in the present embodiment, the enema can be administered twice a day over two weeks. Furthermore, in order to obtain a sufficient effect, it is preferable to take twice a day for 6 weeks. That is, the administration period can be selected from more than 2 weeks and not more than 6 weeks, and is preferably 6 weeks. Here, the week means an approximate period, and even if the administration period increases or decreases for several days due to convenience of administration to a subject, the effect can be obtained, so that the administration period includes approximately ±3 days as a guide. In the present specification, although taking the dose widely refers to administration to the subject, in the embodiment as described later, a method of transanal administration by suppository or the like is included.

Budesonide has two diastereomers of 22R and 22S. The active ingredient of the enema for rectal application according to the present embodiment may be any one of these diastereomers or may be a mixture thereof (for example, a racemate containing approximately equal amounts of both diastereomers). In several pharmacological aspects, since 22R of the two diastereomers of budesonide is more active than 22S, as the active ingredient of the enema for rectal application according to the embodiment, it is preferable to use racemic or 22R diastereomer, and more preferably 22R diastereomer.

Although the enema for rectal application according to the present embodiment is taken twice a day, and the time point of taking the dose within one day is not particularly limited, it is preferable to have an interval at least 6 hours or more and less than one day (24 hours), and more preferable to take in the morning and night. In addition, as much as possible, it is preferable to take after defecation.

In the enema for rectal application according to the present embodiment, it is preferable to take budesonide twice a day in adults within the range of 1.5 to 2.5 mg per dose, and particularly preferable to take budesonide twice a day so as to be 2 mg per dose.

In a case where the enema for rectal application according to the embodiment is a liquid agent, since the stability of budesonide is high, the pH of the liquid agent is preferably 6.0 or less, more preferably 3.0 to 6.0 from the viewpoint of physiological tolerability, and still more preferably 3.5 to 6.0.

In addition, since budesonide has low solubility in water, in a case where the enema for rectal application according to the embodiment is the liquid agent, solvent for dissolving budesonide is preferably an alcohol or a mixed solvent of water and alcohol. Examples of the alcohols include propylene glycol, ethanol, isopropanol, and the like. The alcohol used as the solvent may be only one type, or two types or more of alcohols may be used in mixture. In a case where the mixed solvent of water and alcohol is used, the ratio of alcohols to water is preferably 100:0 to 80:20, more preferably 98:2 to 93:7, in the mass ratio of water:alcohol.

Since the stability of budesonide can be improved, the enema for rectal application according to the present embodiment preferably contains EDTA sodium salt (sodium ethylenediaminetetraacetate) and/or cyclodextrins. As cyclodextrins, β-cyclodextrin, hydroxy-β-cyclodextrin, or γ-cyclodextrin is preferable.

In addition to the above, the enema for rectal application according to the embodiment may contain various pharmaceutically acceptable additives according to the requirements of the preparation. Examples of such additives include pH adjusters, preservatives, thickeners, emulsifiers, and the like. Examples of the pH adjuster include acids such as acetic acid, citric acid, tartaric acid, hydrochloric acid, phosphoric acid and the like; bases such as potassium hydroxide or sodium hydroxide; or a buffer solution such as a hydrochloric acid buffer solution, a phthalate buffer solution, a phosphate buffer solution, a borate buffer solution, an acetate buffer solution or a citrate buffer solution, and the like. Examples of the preservatives include ethanol, chlorobutanol, benzyl alcohol, phenylethanol, sorbic acid, benzoic acid, sodium disulfite, p-hydroxybenzoate, phenol, m-cresol, p-chloro-m-cresol, a quaternary ammonium salt, or a chlorhexidine, and the like. Examples of the thickener include gelatin, tragacanth, pectin, cellulose derivatives (for example, methyl cellulose, hydroxypropyl methyl cellulose, carboxymethyl cellulose sodium, and the like), polyvinylpyrrolidone, polyvinyl alcohol, polyacrylic acids, xanthan gum, or xanthan gum, and the like. Examples of the emulsifier include aliphatic alcohols such as cetearyl alcohol, cetyl alcohol, stearyl alcohol or myristyl alcohol; and polyoxyethylene alkyl ethers such as polyoxyethylene cetostearyl ether or polyoxyethylene lauryl ether, and the like.

The dosage form of the enema for rectal application according to the present embodiment is not particularly limited as long as the enema is transanally administered directly into the intestinal tract. In the embodiment, the enema for rectal application in the form of a foamy shape or a liquid shape can be used, and examples thereof include a rectal foaming agent, an enema agent, a suppository, and the like. The enema agent may be one that can be distributed as a liquid agent or may be prepared by dissolving a tablet containing budesonide in a solvent such as water just before taking. As the enema for rectal application according to the embodiment, a rectal foaming agent or an enema agent is preferable, and the rectal foaming agent is particularly preferable, since the enema can be directly administered into the large intestine from the anus. Here, the foaming agent refers to a mode in which bubbles are formed by an aqueous solution of the liquid agent to form the foams of aggregated bubbles, and the like. The foaming agent is administered by spraying the foam on the subject or the like.

The rectal foaming agent, the enema agent, and the suppositorie containing budesonide as the active ingredient can be prepared by a known method of the related art, except that these are manufactured so that the dose of budesonide is 1.5 to 2.5 mg per dose. Compositions for the treatment or the prevention of relapse of inflammatory bowel disease containing budesonide and the other ingredients described above can be adjusted to the form of the various enemas for rectal application described above. For example, the rectal foaming agent and the enema agent containing budesonide as the active ingredient can be manufactured by the method described in PTL 1. For example, the rectal foaming agent containing budesonide as the active ingredient can be manufactured as follows. Budesonide dissolved in alcohol is added to the solution prepared by dissolving a preservative or an emulsifier necessary for foam formation in a mixed solvent of alcohols or water and alcohols, and mixed. Thereafter, an aqueous solution in which EDTA sodium salt and an acid are dissolved is stirred while homogenizing. The obtained solution is sealed in a gas filling pack equipped with a commercial valve system as a device for single or multiple administrations, and subsequently propellant gas is added. As the propellant gas, hydrocarbons such as isobutane, n-butane or propane/n-butane mixture are preferable. The gas filling pack may further be provided with a plastic applicator chip.

The enema for rectal application according to the present embodiment may be provided for each medicine package of a single dose, but it may be provided by appropriately adjusting the form that is easy to administer twice a day for 6 weeks. For example, an enema foaming agent can be provided by packing a foaming agent of 14 times (for one week) in aluminum cans, or packaging the foaming agent for 2 weeks (for 28 times) in aluminum cans (aerosol). In addition, these may be combined for 2 to 6 weeks. Such packages are easy to appropriately use for prescription for one person.

Since the enema for rectal application according to the embodiment is excellent in the curing effect of the intestinal mucosa, it is preferably used in order to treat inflammatory bowel disease, or to prevent a relapse. Among these, it is preferable to take in order to treat ulcerative colitis or Crohn's disease, or to prevent a relapse. It is more preferable to take in order to treat ulcerative colitis or Crohn's disease in which there is a lesion from a rectum to a sigmoid colon, or to prevent the relapse. The treatment in the embodiment widely refers to improvement of the subject's symptoms. The prevention of relapse in the embodiment widely refers to prevent symptom deterioration (relapse) of the symptoms of the disease completely or to some extent for the subject after improvement. Since inflammation of the mucosa can be further improved by taking the enema for rectal application according to the embodiment than the method of the related art of taking budesonide once a day, it can be expected that patients taking the enema for rectal application according to the embodiment can maintain remission for a longer period of time after taking. In addition, the enema for rectal application according to the embodiment may be taken in order to treat pouchitis which is an inflammation occurring in the ileac pouch (formed in a pouch shape) after total colonic removal of ulcerative colitis, or to prevent a relapse, similarly to budesonide enema of the related art for rectal application (Gionchetti et al., Alimentary Pharmacology & Therapeutics, 2007, vol. 25, p. 1231-1236; Sambuelli et al., Alimentary Pharmacology & Therapeutics, 2002, vol. 16, p. 27-34).

APPLICATION EXAMPLE

Next, the present embodiment will be described in more detail by illustrating an application example, and the like, but the present invention will not be limited thereto.

Application Example 1

Placebo-Controlled Randomized Double-Blind Multicenter Parallel Group Comparative Study Dose responsiveness, efficacy and safety are investigated for patients with active ulcerative colitis when budesonide 2 mg is rectally administered once a day or twice a day for 6 weeks by a double-blind comparative study with placebo as a control (clinical trial number: Japic CTI-132294).

This clinical trial is conducted in compliance with the ethical principles based on the "Declaration of Helsinki", the criteria prescribed in Article 14, paragraph 3 and Article 80, paragraph 2 of the Pharmaceutical Affairs Law, and "Standards for Implementation of Clinical Trials for Pharmaceuticals (GCP)". In addition, prior to the implementation of the clinical trial, ethical, scientific, medical and pharmacological validity of this clinical trial is examined and approved by the clinical trial review committee.

<Test Drug and Control Drug>

For the trial, an aerosol with fixed dose injection type for rectal injection (rectal foaming agent) is used as a test drug, in which 25 mL (1.35 g) of white creamy foam containing 2 mg of budesonide is released by one injection. As a remission induction therapeutic agent of ulcerative colitis in active phase where the lesion is confined to the rectum and sigmoid colon, the aerosol for rectal injection is approved in Europe at a dosage and dose of budesonide 2 mg once a day (trade name: Budenofalk 2 mg/dose rectal foam, manufactured by Dr. Falk Pharma GmbH).

In addition, as a control drug, an aerosol with fixed dose injection type for rectal injection, of which the appearance and weight, and the like are indistinguishable from the test drug, and which does not contain budesonide, is used.

<Subjects>

The subjects are ulcerative colitis patients in active phase, and are divided into a group administered the test drug once a day (hereinafter, once a day group, 54 cases), a group administered the test drug twice a day (hereafter, twice a day group, 55 cases), and a group administered the control drug (hereinafter, placebo group, 56 cases).

<Dose, Administration Method and Administration Period>

The test drug or control drug is rectally administered twice a day (once in the morning and once in the evening), after defecation, if possible. However, for the once a day group of test drug, a control drug is administered in the morning and a test drug is administered in the evening. The number of injections per dose is one, the administration period is 6 weeks, and the drug is administered until the evening before the evaluation. The dose of budesonide in each group is 2 mg/day for the once a day group, 4 mg/day for the twice a day group, and 0 mg/day for the placebo group.

Furthermore, in order to exclude patients whose symptoms improve due to the action of rectal administration (improvement example due to placebo effect) or patients who develop complaints resulting from rectal administration, a pre-observation period in which the control drug is administered twice a day (once in the morning and once in the evening) for one week under a single-blind test is set prior to this administration.

<Results>

Among MMDAI, it is evaluated that patients who had a bloody stool score of 0 points, an endoscopic score of 1 point or less, and a stool frequency score of 0 points or a decrease of 1 point or more from week 0 (time of starting the administration) are in remission. The average value of remission rates in each group (95% confidence interval on both sides) is 20.4% (11.8% to 32.9%) in the placebo group, 50.9% (38.1% to 63.6%) (P=0.0015) in the once a day group, and 48.2% (35.7% to 61.0%) (P=0.0029) in the twice a day group. The point estimate of the odds ratio for the placebo group (95% confidence interval on both sides) in the logistic regression model with model as main effect model, remission rate as objective variable, and administration group and assignment factor as explanatory variables is 3.994 (1.734 to 9.711) in the once a day group, and 3.674 (1.594 to 8.930) in the twice a day group. The lower limit value of 95% confidence interval on both sides exceeds 1 in both groups.

That is, the remission rate in a case where 2 mg of budesonide is administered once a day for 6 weeks and in a case where 2 mg of budesonide is administered twice a day for 6 weeks is significantly higher than that in the placebo group, and the efficacy of this drug for patients with ulcerative colitis in active phase is confirmed.

The patients with MMDAI endoscopic finding score (0=normal or inactive findings, 1=mild (redness, decreased vascular permeability), 2=moderate (significant redness, disappearance of vascular permeability, fragility, erosion), 3=severe (spontaneous bleeding, ulcer)) of 1 or less are evaluated as mucosal remission. The average value (95% confidence interval on both sides) of mucosal remission rates (endoscopic score≤proportion of subjects with 1 point) (%) in each group is 46.3% (33.7% to 59.4%) in the placebo group, 69.1% (56.0% to 79.7%) in the once a day group, and 76.8% (64.2% to 85.9%) in the twice a day group. In addition, the difference point estimate (95% confidence interval on both sides) from the placebo group is 22.8% (4.3% to 39.3%) in the once a day group, 30.5% (12.3% to 46.0%) in the twice a day group. Significant differences are observed in the once a day group and twice a day group as compared with the placebo group. The results are illustrated in Table 1 and FIG. 1. In the table and figure, "budesonide once a day administration group" illustrates the result of once a day group, and "budesonide twice a day administration group" illustrates the result of twice a day group, respectively.

TABLE 1

| | | Placebo group | Budesonide once a day administration group | Budesonide twice a day administration group |
|---|---|---|---|---|
| Analysis target case | | 54 | 55 | 56 |
| Case | | 25 | 38 | 43 |
| Proportion (%) | | 46.3 | 69.1 | 76.8 |
| 95% confidence interval of proportion | | 33.7 to 59.4 | 56.0 to 79.7 | 64.2 to 85.9 |
| Comparison with placebo group | Point estimate of proportion difference | — | 22.8 | 30.5 |
| | 95% confidence interval of proportion difference | — | 4.3 to 39.3 | 12.3 to 46.0 |

Patients with MMDAI endoscopic score of 0 are evaluated as mucosal healing. The average value (95% confidence interval on both sides) of mucosal healing rates (endoscopic score=proportion of subjects with 0 point) (%) in each group is 5.6% (1.9% to 15.1%) in the placebo group, 23.6% (14.4% to 36.3%) (P=0.0159) in the once a day group, and 46.4% (34.0% to 59.3%) (P<0.0001) in the twice a day group. In addition, the difference point estimate (95% confidence interval on both sides) from the placebo group is 18.1% (4.8% to 31.3%) in the once a day group, 40.9% (25.2% to 54.2%) in the twice a day group. Significant differences are observed in the once a day group and twice a day group as compared with the placebo group. Furthermore, the mucosal healing rate is significantly higher in the twice a day group than in the once a day group.

Figure 2:
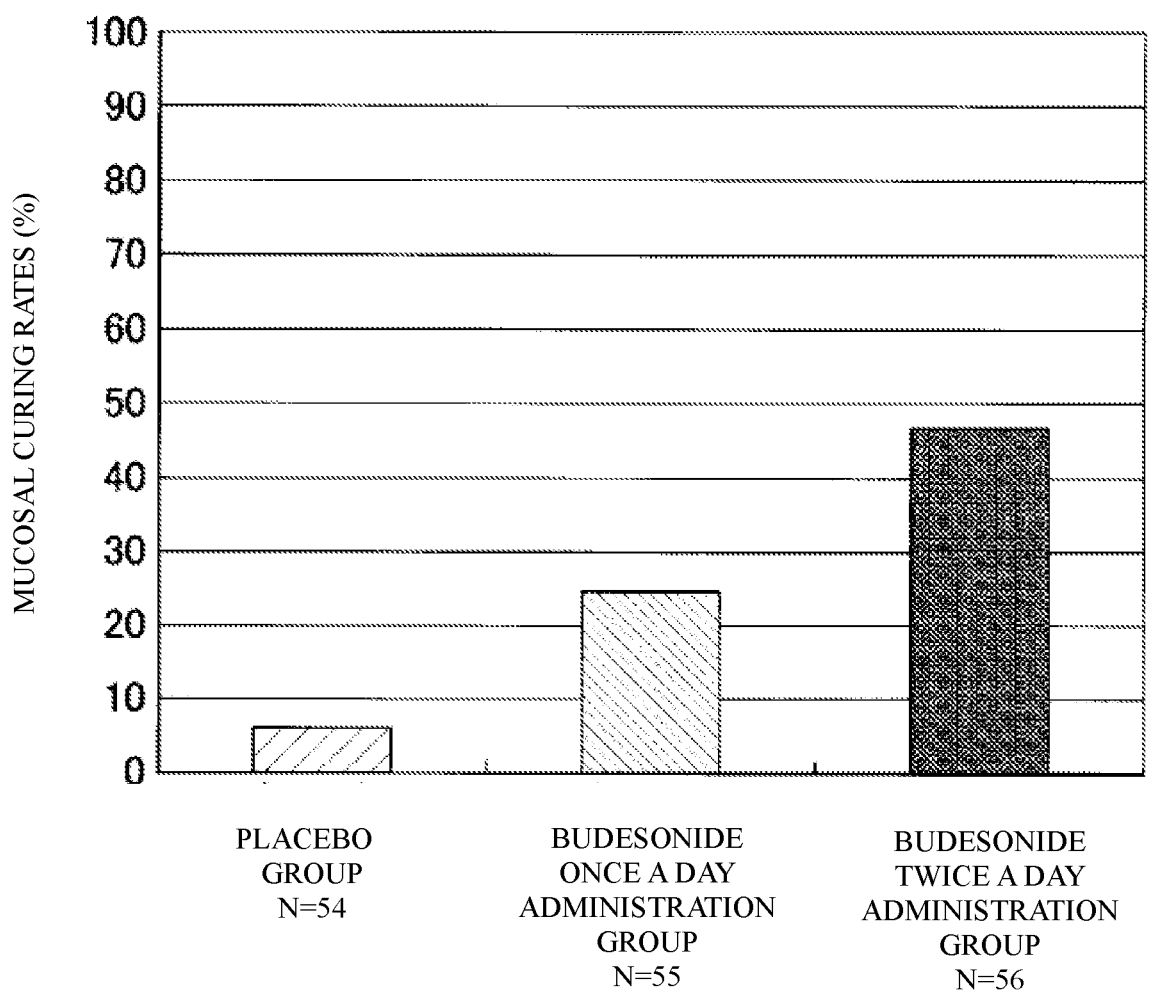
FIG. 2 is a diagram illustrating mucosal curing rates (%) of each group in Application Example 1.

As a result of the analysis in the logistic regression model with mucosal healing rate as objective variable, and administration group and assignment factor as explanatory variables, point estimates of the odds ratio for the once a day group and twice a day group for the placebo group (95% confidence interval on both sides) are respectively 5.143 (1.516 to 23.716) and 15.553 (4.850 to 70.232). The lower limit value of 95% confidence interval on both sides exceeds 1. The results are illustrated in Table 2 and FIG. 2. In the table and figure, "budesonide once a day administration group" illustrates the result of once a day group, and "budesonide twice a day administration group" illustrates the result of twice a day group, respectively.

TABLE 2

|  |  | placebo group | Budesonide once a day administration group | Budesonide twice a day administration group |
| --- | --- | --- | --- | --- |
| Analysis target case |  | 54 | 55 | 56 |
| Case |  | 3 | 13 | 26 |
| Proportion (%) |  | 5.6 | 23.6 | 46.4 |
| 95% confidence interval of proportion |  | 1.9 to 15.1 | 14.4 to 36.3 | 34.0 to 59.3 |
| Comparison with placebo group | Point estimate of proportion difference | — | 18.1 | 40.9 |
|  | 95% confidence interval of proportion difference | — | 4.8 to 31.3 | 25.2 to 54.2 |

On the other hand, regarding safety, serum cortisol decrease and serum corticotropin decrease occurs as adverse events due to administration of the test drug. Although it is indicated that the incidence of adverse events increased in the twice a day group as compared with once a day group, increase in the incidence of adverse events related to glucocorticoids is not observed, and serious adverse events or severe adverse events are not occurred.

From these results, it is considered that tolerability of budesonide 2 mg to patients of ulcerative colitis for rectal administration once a day, 6 weeks or twice a day for 6 weeks is acceptable.

The dosing period of Application Example 1 is illustrated in Table 3. The group administered twice a day is administered for 15 to 45 days, and the group administered for 42 days or more is 78.6%. In consideration of the patient's visit to the hospital, the administration schedule is ±3 days as conformity.

TABLE 3

| Taking period of therapeutic drug | Placebo group | AJG511 once a day administration group | AJG511 twice a day administration group | Total |
| --- | --- | --- | --- | --- |
| 1 to 13 days | 0 (0.0) | 0 (0.0) | 0 (0.0) | 0 (0.0) |
| 14 to 27 days | 1 (19) | 1 (18) | 3 (5.4) | 5 (3.0) |
| 28 to 41 days | 23 (42.6) | 13 (23.6) | 9 (16.1) | 45 (27.3) |
| 42 to 45 days | 30 (55.6) | 41 (74.5) | 44 (78.6) | 115 (69.7) |
| Number of control cases | 54 | 55 | 56 | 165 |
| Average value | 40.9 | 41.7 | 41.0 | 41.2 |
| Maximum value | 45 | 45 | 45 | 45 |
| Median value | 42.0 | 42.0 | 42.0 | 42.0 |
| Minimum value | 16 | 15 | 15 | 15 |

INDUSTRIAL APPLICABILITY

The enema for rectal application according to the present invention has remarkably high healing effect on intestinal mucosa where ulcer and erosion occur due to inflammation. Therefore, the enema for rectal application according to the present invention is extremely excellent as an enema for rectal application in order to treat the inflammatory bowel disease such as ulcerative colitis and Crohn's disease or the like, or to prevent a relapse.

The invention claimed is:

1. A method of treating inflammatory bowel disease or preventing relapse of inflammatory bowel disease by transanally administering to a subject in need thereof an enema comprising 1.5 to 2.5 mg of budesonide twice a day for 6 weeks.

2. The method of claim 1, wherein the enema comprises 2 mg of budesonide per dose.

3. The method of claim 1, wherein the enema has a foamy shape or a liquid shape.

4. The method of claim 1, wherein the administration of twice a day is performed with an interval of at least 6 hours between the first and second administrations.

5. A method of healing intestinal mucosa caused by inflammatory bowel disease by transanally administering to a subject in need thereof an enema comprising 1.5 to 2.5 mg of budesonide twice a day for 6 weeks.

6. The method of claim 5, wherein the enema comprises 2 mg of budesonide per dose.

7. The method of claim 5, wherein the enema has a foamy shape or a liquid shape.

8. The method of claim 5, wherein the administration of twice a day is performed with an interval of at least 6 hours between the first and second administrations.

* * * * *

UNITED STATES PATENT AND TRADEMARK OFFICE
CERTIFICATE OF CORRECTION

| | | |
|---|---|---|
| PATENT NO. | : 12,064,509 B2 | Page 1 of 1 |
| APPLICATION NO. | : 17/581354 | |
| DATED | : August 20, 2024 | |
| INVENTOR(S) | : Yamada et al. | |

It is certified that error appears in the above-identified patent and that said Letters Patent is hereby corrected as shown below:

On the Title Page

Item (30) Foreign Application Priority Data should be added to read JP 2015-012723, filed January 26, 2015.

Signed and Sealed this
Twenty-sixth Day of November, 2024

Katherine Kelly Vidal
*Director of the United States Patent and Trademark Office*